(12) United States Patent
Amelink et al.

(10) Patent No.: US 7,937,226 B2
(45) Date of Patent: May 3, 2011

(54) METHOD AND DEVICE FOR BACKSCATTER SPECTROSCOPY

(75) Inventors: Arjen Amelink, Gouda (NL); Henricus Josephus Cornelis Maria Sterenborg, Capelle aan den IJssel (NL)

(73) Assignees: Erasmus University Medical Center, Roherdam (NL); Stichting voor de Technische Wetenschappen, Utrecht (NL)

( * ) Notice: Subject to any disclaimer, the term of this patent is extended or adjusted under 35 U.S.C. 154(b) by 349 days.

(21) Appl. No.: 10/573,337

(22) PCT Filed: Sep. 22, 2004

(86) PCT No.: PCT/NL2004/000657
§ 371 (c)(1),
(2), (4) Date: Feb. 21, 2007

(87) PCT Pub. No.: WO2005/029051
PCT Pub. Date: Mar. 31, 2005

(65) Prior Publication Data
US 2008/0004842 A1 Jan. 3, 2008

(30) Foreign Application Priority Data
Sep. 23, 2003 (EP) .................. 03078010

(51) Int. Cl.
*G01N 31/00* (2006.01)
(52) U.S. Cl. .................................................. 702/23

(58) Field of Classification Search ............. 702/23
See application file for complete search history.

(56) References Cited

U.S. PATENT DOCUMENTS

| 5,949,077 A | * | 9/1999 | Alfano et al. ........ 250/459.1 |
| 6,381,018 B1 | * | 4/2002 | Bigio et al. ............... 356/432 |
| 2002/0171831 A1 | | 11/2002 | Backman et al. |
| 2009/0326384 A1 | * | 12/2009 | Bigio et al. .............. 600/476 |

OTHER PUBLICATIONS

International Search Report of PCT/NL2004/000657, dated Jan. 28, 2005.

* cited by examiner

*Primary Examiner* — Aditya Bhat
(74) *Attorney, Agent, or Firm* — Abelman, Frayne & Schwab

(57) ABSTRACT

A method and a device determine a physical property of a medium, such as a concentration of a substance in the medium. The device includes a light source; a probe with optical fibers positioned alongside each other, with a first optical fiber delivering radiation from the light source to a sample and collecting first backscattered radiation from the sample, and with a second optical fiber collecting second backscattered radiation; a spectrometer for producing first and second signals based on the first and second backscattered radiation; and a processor which determines a differential backscatter signal from the first and second signals and to calculate the physical property by curve fitting the measured differential backscatter signal to a backscatter function. Depending on whether the diameter of the optical fibers is smaller or greater than the mean free path of photons in the sample, different backscatter functions are used.

16 Claims, 9 Drawing Sheets

METHOD AND DEVICE FOR BACKSCATTER SPECTROSCOPY

CROSS-REFERENCE TO RELATED APPLICATIONS

This application is a 371 of international application number PCT/NL2004/000657, filed on Sep. 22, 2004.

BACKGROUND OF THE INVENTION

1. Field of the Invention

The present invention relates to a method of determining of a physical feature of a medium, comprising: producing radiation with a light source; placing a probe on a sample of the medium, the probe comprising a first optical fiber having a first diameter, and at least a second optical fiber having a second diameter; sending light coming from the light source, through the first optical fiber; collecting first backscattered radiation through the first optical fiber and second backscattered radiation through the second optical fiber; producing a first signal based on the first backscattered radiation, and a second signal based on the second backscattered radiation; and determining a measured differential backscatter signal as a function of wavelength using the first and second signals.

2. Description of the Related Art

Such a method is known, as described in A. Amelink, M. P. L. Bard, J. A. Burgers, and H. J. C. M. Sterenborg, "Single Scattering Spectroscopy for the Endoscopic Analysis of Particle Size in Superficial Layers of Turbid Media", Applied Optics 42, pp. 4095-4101 (2003); which describes a special device used to determine particle sizes in superficial layers. The device is suitable for measuring particle sizes in, for example, an aqueous suspension with polystyrene spheres, but is not fitted to accurately measure particle sizes in living tissue. So, determining whether living tissue is normal or precancerous, by way of measuring particle sizes in living tissue is not very promising.

As described in R. M. P. Doornbos, R. Lang, M. C. Aalders, F. W. Cross, and H. J. C. M. Sterenborg, "The Determination of In Vivo Human Tissue Optical Properties and Absolute Chromophore Concentrations Using Spatially Resolved Steady-State Diffuse Reflectance Spectroscopy", Phys. Med. Biol. 44 (1999), pp. 967-981; the optical properties of human tissue are determined in vivo using a spectroscopic arrangement with ten optical fibers. One of the fibers is used to irradiate a sample, and nine other fibers collect the reflected light. By using a multitude of fibers to collect the reflected light, it is possible to calculate scattering and absorption coefficients of the sample. However, the method is not suitable for locally measuring the optical properties of the tissue. In particular, only mean values of the absorption coefficient of a relatively large part of the sample can be determined.

BRIEF SUMMARY OF THE INVENTION

It is an object of the present invention to locally measure a physical feature, such as a concentration, of a substance in a medium.

The object is achieved by a method as described above, characterized by calculating the physical feature by curve fitting the measured differential backscatter signal to a backscatter function, in which the backscatter function is a function of an average path-length traveled by detected scattered photons, wherein the average path-length is independent from an absorption coefficient of the medium, and from a scattering coefficient of the medium. Contrary to methods using diffusely scattered photons such as described in Doornbos et al. cited herein, in the method according to the invention, the local absorption coefficient of the sample is measured in an absolute way, independent of the magnitude of the local scattering and absorption coefficients. This facilitates the measurement of absolute concentrations of absorbing molecules in a sample without requiring prior knowledge of the magnitude of the scattering and absorption coefficients of the medium.

In an example embodiment, the average path-length is proportional to the first fiber diameter. This has as additional advantage that the average path-length and thereby the average penetration depth into the sample of the photons that contribute to the differential backscatter signal can be controlled by choosing the fiber diameter. As a result, the sampling volume can be controlled by adjusting the fiber diameter. Hence, the fiber optic probe can be engineered to match the relevant dimensions of the medium under investigation.

In a particular embodiment, the physical feature is a concentration of at least one substance in the medium.

The invention also relates to a device for determining a physical feature of a medium, comprising: a light source for producing radiation; a probe with at least a first and a second optical fiber, the first optical fiber having a first diameter and being arranged to deliver the radiation on a sample of the medium and to collect first backscattered radiation from the sample, the second optical fiber having a second diameter and being arranged to collect second backscattered radiation, wherein the second optical fiber is positioned alongside the first optical fiber; a spectrometer for producing a first signal based on the first backscattered radiation, and for producing a second signal based on the second backscattered radiation; a processor arranged to determine a measured differential backscatter signal as a function of wavelength using the first and second signals, characterized in that the processor is arranged to calculate the physical feature by curve fitting the measured differential backscatter signal to a backscatter function, in which the backscatter function is a function of an average path-length traveled by detected scattered photons, the average path-length being independent from an absorption coefficient of the medium, and from a scattering coefficient of the medium.

Furthermore, the invention relates to a computer program and a data carrier provided with a product including the computer program and enabled to calculate a physical feature by curve fitting a measured differential backscatter signal to a backscatter function using an average path-length as described herein.

In another aspect of the invention, the invention relates to a method of determining a physical feature of a medium, comprising: producing radiation with a light source; placing a probe on a sample of the medium, the probe comprising a first optical fiber having a first diameter, and at least a second optical fiber having a second diameter; sending light coming from the light source, through the first optical fiber; collecting first backscattered radiation through the first optical fiber and second backscattered radiation through the second optical fiber; producing a first signal based on the first backscattered radiation, and a second signal based on the second backscattered radiation; and determining a measured differential backscatter signal as a function of wavelength using the first and second signals, characterized by calculating the physical feature by curve fitting the measured differential backscatter signal to a backscatter function, in which the backscatter function is a function of a mean free path of photons. In this method, it is assumed that only singly scattered photons contribute to the differential backscatter signal and as a result the backscatter function can be easily derived analytically.

In an example embodiment, the physical feature is a concentration of at least one substance in the medium.

The invention also relates to a device for determining a physical feature of a medium with a processor arranged to calculate the physical feature by curve fitting a measured differential backscatter signal to a backscatter function using a mean free path as described herein.

Furthermore, the invention relates to a computer program and a data carrier provided with a product including the computer program and enabled to calculate a physical feature by curve fitting a measured differential backscatter signal to a backscatter function using a mean free path as described herein.

Finally, the invention relates to a method for simultaneously measuring backscatter radiation on different locations of a sample; determining a physical feature for the different locations; and calculating a standard deviation of the physical feature.

BRIEF DESCRIPTION OF THE SEVERAL VIEWS OF THE DRAWINGS

The present invention will be described below with reference to exemplary embodiments and the accompanying schematic drawings, in which.

DETAILED DESCRIPTION OF THE INVENTION

The present invention is related to international application number PCT/NL2004/000657, filed on Sep. 22, 2004, which is incorporated herein by reference in its entirety.

Figure 1:
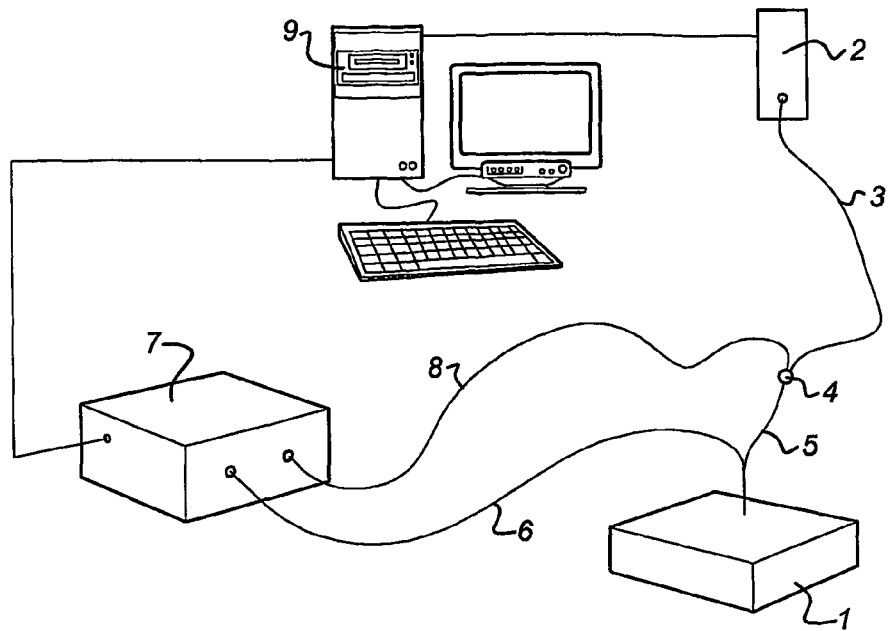
FIG. 1 is a schematic diagram of a measuring device according to a preferred embodiment.

A schematic diagram of a preferred embodiment according to the invention is shown in FIG. 1. The setup consists of a set of optical fibers for the delivery and collection of light to and from a sample 1 under investigation. Light from a light source 2, for example a Tungsten Halogen lamp (Avantes HL-2000-FHSA), is led through a first arm 3 of a bifurcated optical fiber. The bifurcated optical fiber is at a distal end 4 coupled to a first distal end of a delivery-and-collection fiber 5 (in the following referred to as dc-fiber) which is small enough to be fit through a working channel of a clinical endoscope, not shown. A second distal end of the delivery-and-collection fiber 5 contacts the sample 1. Alongside the dc-fiber 5, a collection fiber 6 is arranged to collect light reflected by the sample 1. The collection fiber 6 (referred to as c-fiber 6) is connected to a slave channel of a dual-channel spectrometer 7, for example an Avantes SD2000. Preferably, the dc-fiber 5 is polished at a small angle to reduce specular reflections.

Light reflected back from the sample 1 into the c-fiber 6 is led directly into the slave channel of the dual-channel spectrometer 7. A second arm 8 of the bifurcated fiber is connected to a master channel of the dual-channel spectrometer 7. Light reflected into the dc-fiber 5 is coupled back into the bifurcated fiber, and reaches the dual-channel spectrometer 7 via the second arm 8 of the bifurcated fiber. An output of the spectrometer 7 is connected to an input of a processor 9 which is arranged to analyze signals from the spectrometer 7.

If only the dc-fiber 5 is used to deliver and collect light to and from the sample 1, a large fraction of collected light is due to single backscattering from small sample depths, as described in Amelink et al. cited herein. A single-to-multiple scattering ratio depends on the scattering coefficient and phase function of the sample 1 and on a diameter of the dc-fiber 5. The contribution of multiply scattered light to the signal of the dc-fiber 5 can be approximately determined by combining the signal of the dc-fiber 5 with a signal coming from an additional fiber, i.e. the c-fiber 6 mentioned above.

As described in H. C. van de Hulst, "Light Scattering by Small Particles", Wiley, New York, 1957; a differential backscatter signal $R_{bs}$ as a function of the wavelength k is determined using a formula like $$R_{bs}(\lambda) = c \cdot \left( \frac{(I(\lambda) - I_n(\lambda))}{(I_{white}(\lambda) - I_{black}(\lambda))} - \frac{J(\lambda)}{(J_{white}(\lambda) - J_{black}(\lambda))} \right) \quad (1)$$

where I(λ) is the signal from the dc-fiber 5 in contact with the sample 1, $I_n(\lambda)$ is the signal from the dc-fiber 5 submersed in a fluid with an appropriate refractive index (for tissue: water would be appropriate), $I_{white}(\lambda)$ is the signal from the dc-fiber 5 with the probe-tip at a specific distance from a diffuse reflecting reference material with a large, preferably wavelength-independent reflectance coefficient (white spectralon) and $I_{black}(\lambda)$ is the signal from the dc-fiber 5 with the probe-tip at that same specific distance from a diffuse reflecting reference material with a small, preferably wavelength-independent reflectance coefficient (black spectralon). Furthermore, J(λ) is the signal from the c-fiber 6 in contact with the sample 1 and $J_{white}(\lambda)$ and $J_{black}(\lambda)$ are the signals from the c-fiber 6 with the probe-tip at the previously mentioned specific distance from the white or black spectralons, respectively. Finally, c is a calibration constant that depends on the distance between the probe-tip and the reference materials.

According to the invention, the processor 9 is arranged to calculate the physical feature using a predefined mathematical model, the differential backscatter signal ($R_{bs}$) and a curve fitting mechanism. In an example embodiment, the diameter of the fibers 5, 6 are selected depending on a mean free path (mfp) of photons sent into the sample 1. It is noted that if the mean free path cannot be estimated before selecting a fiber diameter, initially two arbitrary fiber diameters may be selected. After curve fitting the measuring results using two different mathematical models, it will show which model applies.

Figure 2A:
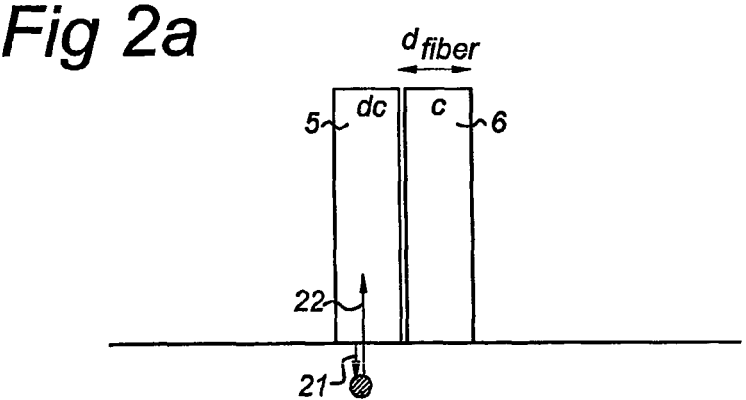
FIGS. 2a and 2b show cross-sections of a sample and two fiber tips in the situation wherein the mean free path of the photons is much larger than the diameter of the fibers.
Figure 2B:
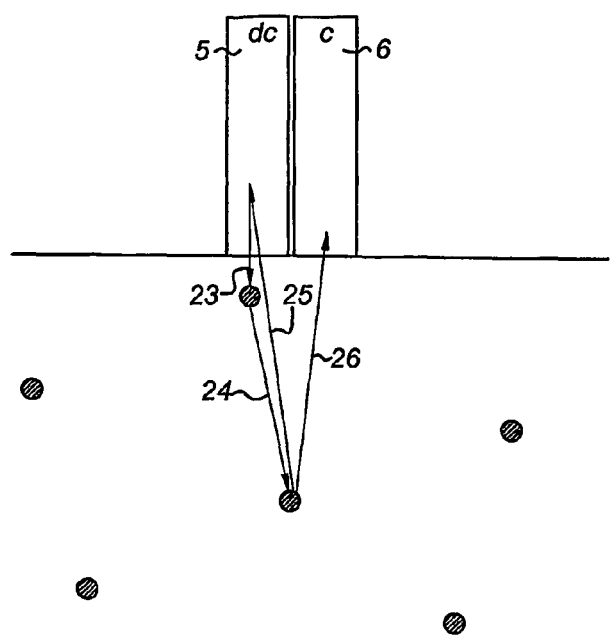

FIGS. 2a and 2b depict fiber tips of the dc-fiber 5 and the c-fiber 6 in the situation wherein the mean free path (mfp) of photons coming out of the dc-fiber 5 is much larger than a diameter fiber of the fibers 5, 6. In an example embodiment, the diameters of both fibers 5, 6 are of equal size. However it should be understood that other selections are possible. In FIG. 2a, lines 21 and 22 show an example of a path traveled by a detectable singly scattered photon. In FIG. 2b, lines 23, 24, 25 and lines 23, 24, 26 show two possible paths of detectable multiply scattered photons. All multiple scattering events occur at such large distances from the fiber tip of the fibers 5, 6 that the probability of detection of multiply scattered photons is roughly equal for the dc-fiber 5 and the c-fiber 6. The differential backscatter signal $R_{bs}(\lambda)$ will now purely be determined by singly scattered photons.

In an example embodiment, the respective diameters of the fibers 5, 6 are selected so that mfp>$d_{fiber}$. In the predefined mathematical model of this embodiment, the differential backscatter signal $R_{bs}(\lambda)$ is an exponential function of two times the mean free path. Below, an explanation for this model is given.

In the absence of absorbers, the differential backscatter signal $R_{bs}(\lambda)$ is proportional to the local, superficial scattering coefficient $\mu_s(\lambda) = Q_{sca}(\lambda) \cdot \rho \cdot As$:

$$R_{bs}(\lambda) = C_{app} \cdot \frac{1}{4\pi} \cdot \int_{\Omega_{NA}} d\Omega \cdot p(\lambda, \Omega) \cdot Q_{sca}(\lambda) \cdot \rho \cdot As \quad (2)$$

where $C_{app}$ is an apparatus constant that depends amongst others on the distance between the probe tip and the reference materials (black and white spectralon), $p(\lambda, \Omega)$ is a function called the phase function where $\Omega$ is the scattering angle, $Q_{sca}(\lambda)$ is the scattering efficiency, $\rho$ is the concentration of substances present in the sample 1, and As is the area of a scattering particle. For example, using a fused silica fiber with numerical aperture NA=0.22, the differential backscatter signal $R_{bs}(\lambda)$ can be approximated by $$R_{bs}(\lambda) \approx C_{app} \cdot \frac{1}{4\pi} \cdot \int_0^{2\pi} d\varphi \cdot \int_{170}^{180} d\theta \cdot \sin(\theta) \cdot \quad (3)$$
$$p(\lambda, 180) \cdot \mu_s(\lambda)$$
$$= C'_{app} \cdot p(\lambda, 180) \cdot \mu_s(\lambda)$$

where $\varphi$ is the azimuthal angle and $\theta$ is the polar angle.

Figure 3:
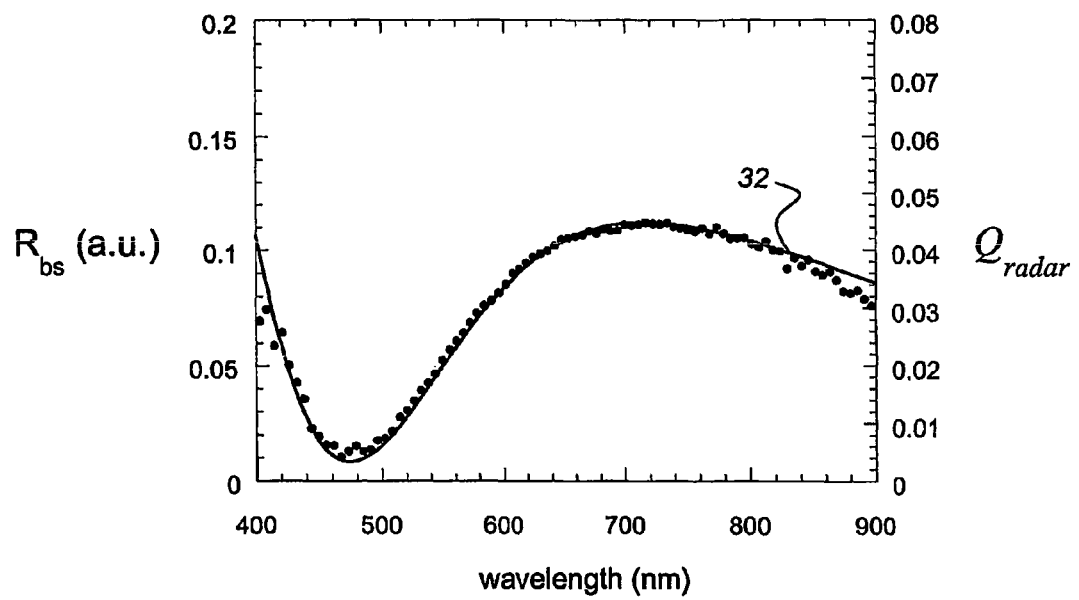
FIG. 3 shows the results of Monte Carlo simulations for a homogeneous medium.

FIG. 3 shows the differential backscatter signal $R_{bs}(\lambda)$ of measurements (see dots in FIG. 3) of a dilute suspension of 0.2 μm polystyrene spheres along with a calculation (see curve 32) according to Eq. (3). In FIG. 3 $R_{bs}(\lambda)$ is shown using arbitrary units (a.u.). Also a value of $Q_{radar}$ where $Q_{radar} = 4\pi \cdot p(\lambda, 180) \cdot Q_{sca}(\lambda)$, is indicated in the figure. FIG. 3 shows excellent agreement between the measurement (i.e. the dots) and the calculation, which indicates that if mfp>$d_{fiber}$, the single scattering is indeed the dominant contributor to the differential backscatter signal $R_{bs}(\lambda)$ as defined in Eq. (1).

A singly scattered photon first travels from the tip of the dc-fiber 5 to a particle, and then (the same distance) back from the particle to the tip of the dc-fiber 5 (or tip of c-fiber 6), see also FIG. 2a. So an average path length $\tau(\lambda)$ traveled by the measured single scattered photons is equal to two times the mean free path mpf($\lambda$), i.e.

$$\tau(\lambda) = 2 \cdot mfp(\lambda) \quad (4)$$

In the presence of n absorbing species with specific absorption coefficients, $\mu_a^{spec,i}(\lambda)$, the differential backscatter signal becomes $$R_{bs} = C'_{app} \cdot p(\lambda, 180) \cdot \mu_s(\lambda) \cdot \exp\left(-\tau(\lambda) \cdot \sum_{i=1}^{n} \rho_i \cdot \mu_a^{spec,i}(\lambda)\right) \quad (5)$$
$$= C'_{app} \cdot p(\lambda, 180) \cdot \mu_s(\lambda) \cdot \exp(-2 \cdot mfp(\lambda)) \cdot$$
$$\sum_{i=1}^{n} \rho_i \cdot \mu_a^{spec,i}(\lambda))$$

where $C_{app}'$ is an apparatus constant, $p(\lambda, 180)$ is the phase function, $\mu_s(\lambda)$ is the scattering coefficient of the medium, $\lambda$ is the wavelength of the first and second backscattered radiation, mfp($\lambda$) is the mean free path as a function of the wavelength, n is the number of substances in the sample 1, $\rho_i$ is the concentration of absorber i present in a detection volume of the sample 1, and $\mu_a^{spec,i}(\lambda)$ is the absorption coefficient of absorber i as a function of the wavelength.

It is noted that in Eq. (5) the assumption is made that absorbers are homogeneously distributed and do not influence each other. The Eq. (5) may be corrected for non-linear phenomena such as an inhomogeneous distribution of absorbers, see e.g. R. L. P. van Veen, W. Verkruysse, and H. J. C. M. Sterenborg, "Diffuse Reflectance Spectroscopy from 500 to 1060 nm Using Correction for Inhomogeneously Distributed Absorbers", Opt. Lett. 27, pp. 246-248 (2002).

According to an example embodiment, the specific absorption coefficients of the absorbers, the wavelength dependency of the scattering coefficient $\mu_s$ and the phase function p, together with Eq. (5), are used in order to calculate the concentrations of all the absorbing substances present in the detection volume of the sample 1. Since the detection volume is typically very small in the present invention, the extracted concentrations are highly spatially resolved. This is not possible with the known methods that are based on diffuse reflectance, and wherein the obtained concentrations are averages over large sample volumes, see e.g. Doornbos et al. cited herein.

The apparatus constant $C_{app}'$ (Eq. 3) can be determined for a specific distance between the tip of the dc-fiber 5 and the reference materials (black and white spectralon). For a suspension of monodisperse polystyrene spheres of known size and concentration, the scattering coefficient $\mu_s$ and the phase functional p(180) can be calculated using Mie theory as described in the van de Hulst article cited herein. The apparatus constant $C_{app}'$ simply follows from Eq. (3). In terms of the volume fraction f of the suspension, the radius of the spheres a and the radar efficiency coefficient $Q_{radar}(\lambda) = 4\pi \cdot p(\lambda, 180) Q_{sca}(\lambda)$ the apparatus constant is determined by $$R_{bs}(\lambda) \approx C'_{app} \cdot p(\lambda, 180) \cdot \mu_s(\lambda) \quad (6)$$

$$= C'_{app} \cdot 0.05968 \cdot \frac{f}{a} \cdot Q_{radar}(\lambda)$$

According to another embodiment, the selected diameter $d_{fiber}$ is chosen so that the mean free path is smaller than $d_{fiber}$. In this embodiment, the differential backscatter signal $R_{bs}$ is a function of the fiber diameter fiber $d_{fiber}$. This will be discussed in more detail below.

Figure 4:
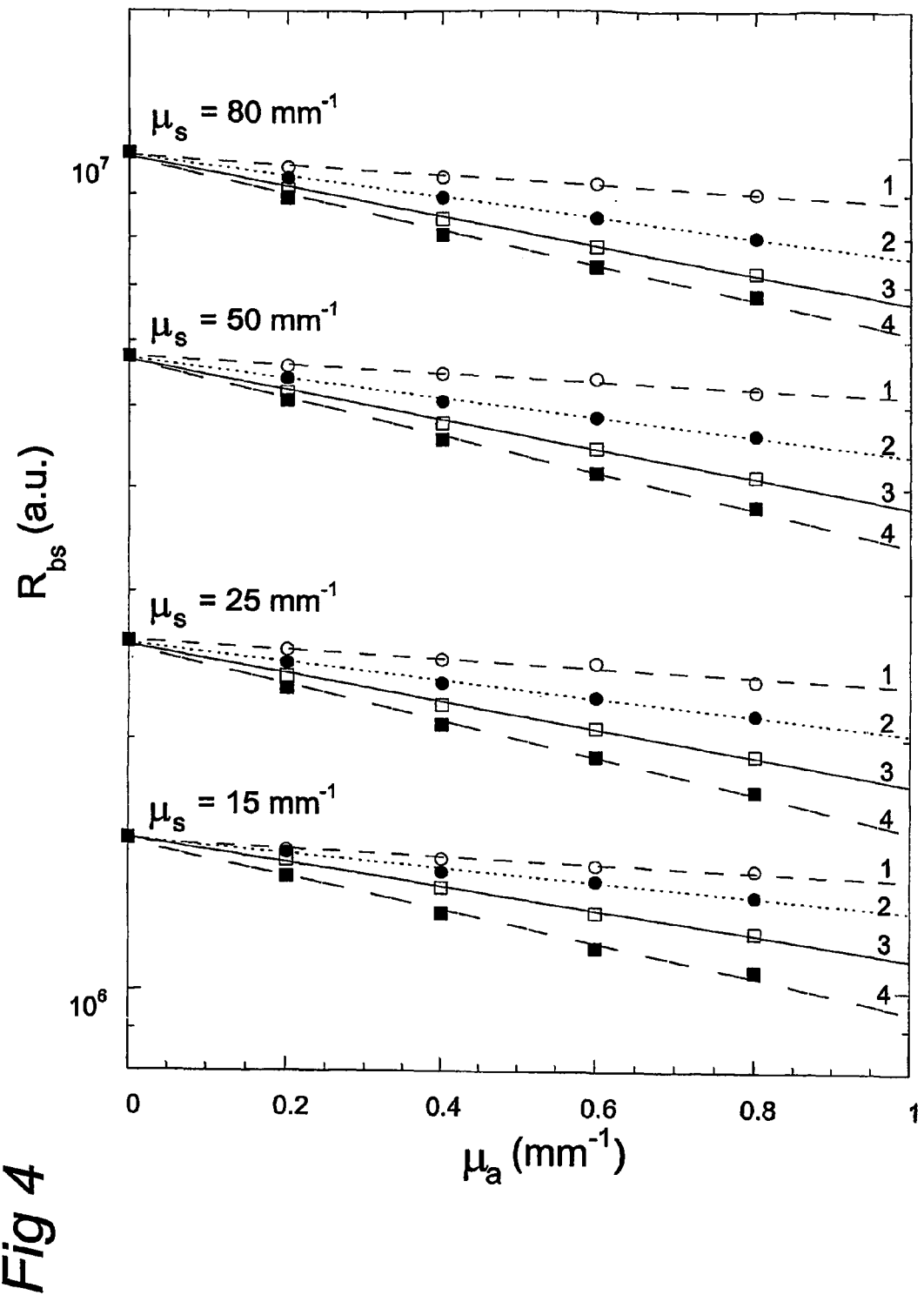
FIG. 4 shows a differential backscatter signal normalized at zero absorption for several scattering coefficients.

When the mean free path of the photons is smaller than the selected fiber diameter (i.e. $mfp(\lambda) < d_{fiber}$), the contribution of multiply scattered light to the differential backscatter signal $R_{bs}(\lambda)$ of the single dc-fiber 5 cannot completely be removed using Eq. (1). In this case, it appears that the average path length of the photons contributing to the signal $R_{bs}(\lambda)$ becomes nearly independent of the optical properties of the sample 1. In this situation, multiple scattering events already occur at small distances from the tip of the dc-fiber 5. An analytical expression for the backscatter signal $R_{bs}(\lambda)$ is not available for this situation and Monte Carlo simulations were used to model the behavior of $R_{bs}(\lambda)$ as a function of the diameter of the fibers 5, 6 and of the optical properties of the sample 1. FIG. 4 shows the results of Monte Carlo simulations using the MCML-code (Monte Carlo for Multi-Layered media) described in L-H Wang, S. L. Jacques, L-Q Zheng, "MCML—Monte Carlo Modeling of Photon Transport in Multi-Layered Tissues", Computer Methods and Programs in Biomedicine 47, pp. 131-146 (1995); and L-H Wang, S. L. Jacques, L-Q Zheng, "CONV—Convolution for Responses to a Finite Diameter Photon Beam Incident on Multi-Layered Tissues", Computer Methods and Programs in Biomedicine 54, pp. 141-150 (1997); for a homogeneous medium with an anisotropy value g=0.9. A flat circular incident beam with diameter $d_{fiber}$ is directed onto the sample 1, and the differential backscatter signal $R_{bs}$ is calculated by subtracting the total reflectance in the c-fiber 6 (with diameter $d_{fiber}$ and center located at a distance $d_{fiber}$ from the center of the incident beam) from the total reflectance in the dc-fiber 5 (with diameter $d_{fiber}$ overlapping the incident beam). Simulations were performed for sets of four different scattering coefficients ($\mu_s$=15, 25, 50 and 80 mm$^{-1}$), four different fiber diameters ($d_{fiber}$=200, 400, 600 and 800 μm) and five different absorption coefficients ($\mu_a$=0, 0.2, 0.4, 0.6 and 0.8 mm$^{-1}$).

Figure 5:
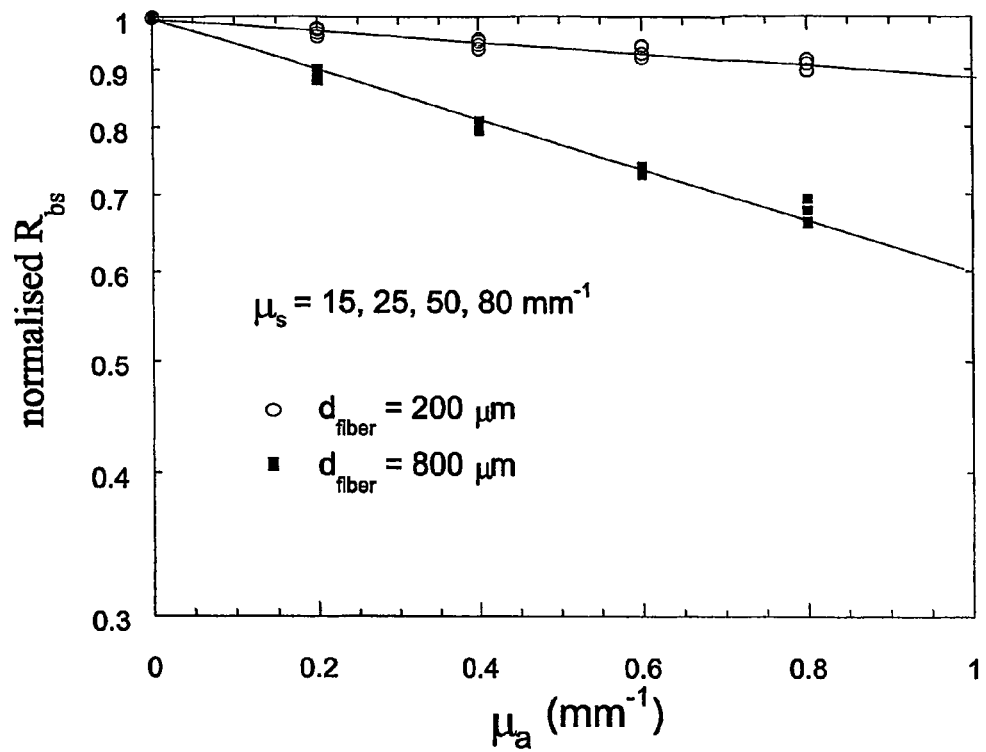
FIG. 5 shows a differential backscatter signal of a dilute suspension of 0.2 μm polystyrene spheres.

FIG. 4 shows $R_{bs}$ as a function of absorption coefficient $\mu_a$ where the open circles/dashed lines correspond to $d_{fiber}$=200 μm, the filled circles/dotted lines correspond to $d_{fiber}$=400 μm, the open squares/solid lines correspond to $d_{fiber}$=600 μm and the filled squares/dash-dotted lines correspond to $d_{fiber}$=800 μm. The differential backscatter signal $R_{bs}$ for each scattering coefficient $\mu_s$ was normalized to the ($d_{fiber}$=200 μm, $\mu_a$=0 mm$^{-1}$) case. FIG. 4 shows that in the absence of absorption, i.e. $\mu_a$=0, the differential backscatter signal $R_{bs}$ depends linearly on the scattering coefficient, $\mu_s$. Furthermore, the slope of the straight lines (signifying the relation between $R_{bs}$ and $\mu_a$) depends only on the fiber diameter and is independent of the scattering coefficient $\mu_s$. The latter is more clearly demonstrated in FIG. 5, where the differential backscatter signal $R_{bs}$ is normalized to unity at zero absorption for all scattering coefficients $\mu_s$. The open circles correspond to $d_{fiber}$=200 μm and the filled squares correspond to $d_{fiber}$=800 μm. These Monte Carlo simulations therefore suggest that in the situation where $mfp < d_{fiber}$, the diameter of the fibers 5, 6 determines the average path length τ of the measured photons. The backscatter signal $R_{bs}$ for this range of parameters can thus be written as $$R_{bs}(\lambda) = C_1 \cdot \mu_s \cdot \exp(-\tau \cdot \mu_s) = C_1 \cdot \mu_s \cdot \exp(-C_2 \cdot d_{fiber} \cdot \mu_a) \quad (7)$$

where $C_1$ and $C_2$ are constants, τ is the average path length, $\mu_a$ is the absorption coefficient, $\mu_s$ is the scattering coefficient and $d_{fiber}$ is the fiber diameter of the fibers 5, 6.

An exact analytical expression for $R_{bs}(\lambda)$ is not available due to the large contribution of multiple scattering events to the signal. Measurements were done for determining a total integrated backscatter signal $R_{tot}$ for a range of λ between 400-900 nm, using the formula $$R_{tot}(\mu_s) = \int_{400\ nm}^{900\ nm} d\lambda R_{bs}(\lambda, \mu_s) \quad (8)$$

Figure 6:
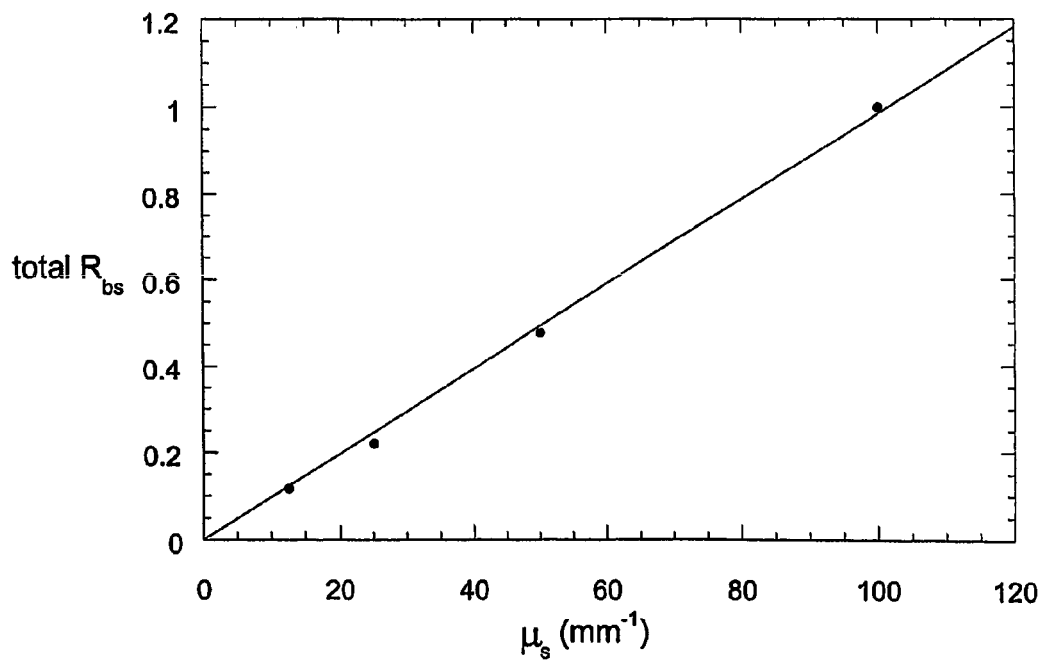
FIG. 6 shows the total differential backscatter signal as a function of the reflection coefficient $\mu_s(\lambda)$ in the range of 10-100 $mm^{-1}$.

FIG. 6 shows that the integrated total backscatter signal $R_{tot}(\mu_s)$ is proportional to $\mu_s(\lambda)$ in the relevant range of, between 10-100 mm$^{-1}$. Therefore, in the absence of absorbers, it follows that $$R_{bs}(\lambda) = C_{app} \cdot \mu_s(\lambda) \quad (9)$$

which is in agreement with the Monte Carlo simulations.

In the presence of n absorbing substances in a suspension, with specific absorption coefficients $\mu_a^{spec,i}(\lambda)$, the differential backscatter signal becomes $$R_{bs} = C_{app} \cdot \mu_s(\lambda) \cdot \exp\left(-\tau \cdot \sum_{i=1}^{n} \rho_i \cdot \mu_a^{spec,i}(\lambda)\right) \quad (10)$$

where τ is the average path length of the detected backscattered photons and $\rho_i$ is the concentration of the substance i.

Non-linear phenomena such as an inhomogeneous distribution of absorbers are not incorporated in Eq. (10), but can be added by the skilled person, see e.g. the van Veen et al. article cited herein.

Figure 7:
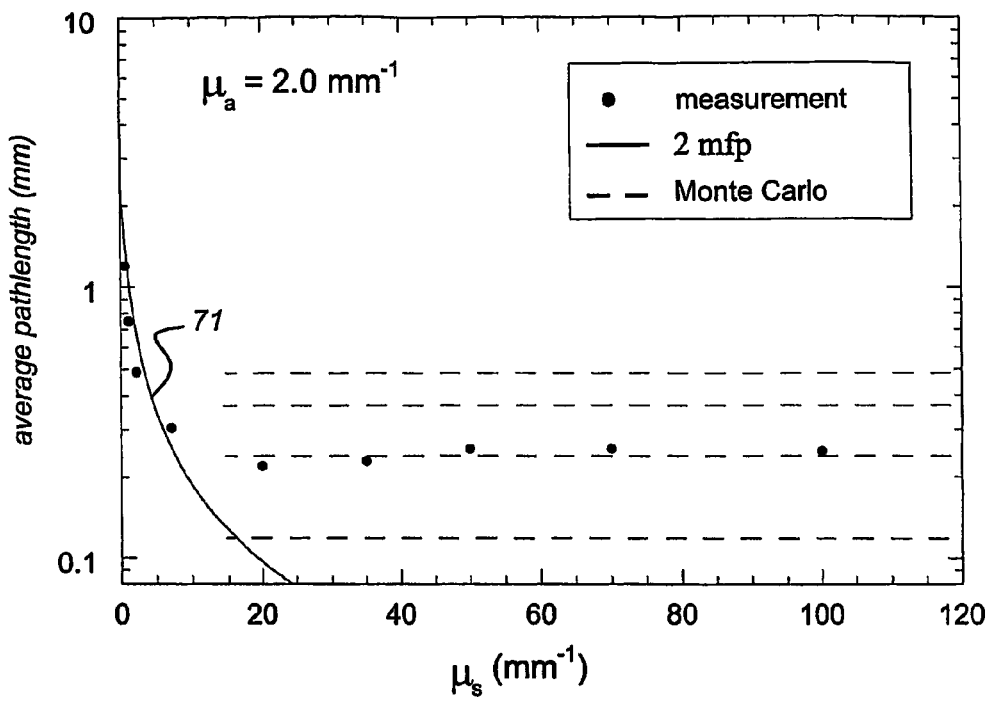
FIG. 7 shows the measured and calculated average path length τ as a function of the average scattering coefficient.

FIG. 7 shows the measured and calculated average path length τ as a function of the average scattering coefficient $<\mu_s(\lambda)>$ (with 500 nm<λ<700 nm) for $d_{fiber}$=0.4 mm and for absorption coefficient $\mu_a(\lambda)$=2.0 mm$^{-1}$ at λ=600 nm. In FIG. 7 measurements are indicated by dots, the τ=2·mfp curve is indicated by a line 71 and Monte Carlo simulations are depicted by dashed lines. Identical results were obtained for suspensions with an absorption coefficient of $\mu_a$=1.0 mm$^{-1}$ at 600 nm. The average path length τ was determined using suspensions of polystyrene spheres with different sizes and concentrations to vary the scattering coefficient $\mu_s(\lambda)$. The anisotropy g of these suspensions was in the range of 0.8-0.9. Evans Blue dye was added as an absorber, and the average path length τ was calculated from Eqs. (9) and (10) and knowledge of the concentrations and a specific absorption coefficient of Evans Blue, as will be known to the skilled person.

Looking at the measured average path lengths of FIG. 7, it clearly shows that for large scattering coefficients ($\mu_s$=10-100 mm$^{-1}$ the range relevant for tissue) the average path length τ is independent of the scattering coefficient $\mu_s$ to within 10% and approximately equal to half the fiber diameter (τ≈0.24 mm while $d_{fiber}$=0.40 mm), in agreement with the Monte Carlo simulations (the dashed lines correspond to Monte Carlo calculations for $d_{fiber}$=0.2, 0.4, 0.6 and 0.8 mm). For small scattering coefficients (e.g. $\mu_s$<5 mm$^{-1}$) the average path length τ is well described by τ=2·mfp, according to Eq. (4), see line 71. FIG. 7 also clearly demonstrates that the transition from the 'single scattering regime' to the 'constant path length regime' occurs for mean free paths of the order of the fiber diameter. It is therefore expected that single scattering will prevail over a larger range of scattering coefficients for fiber diameters smaller than 400 μm.

Figure 8:
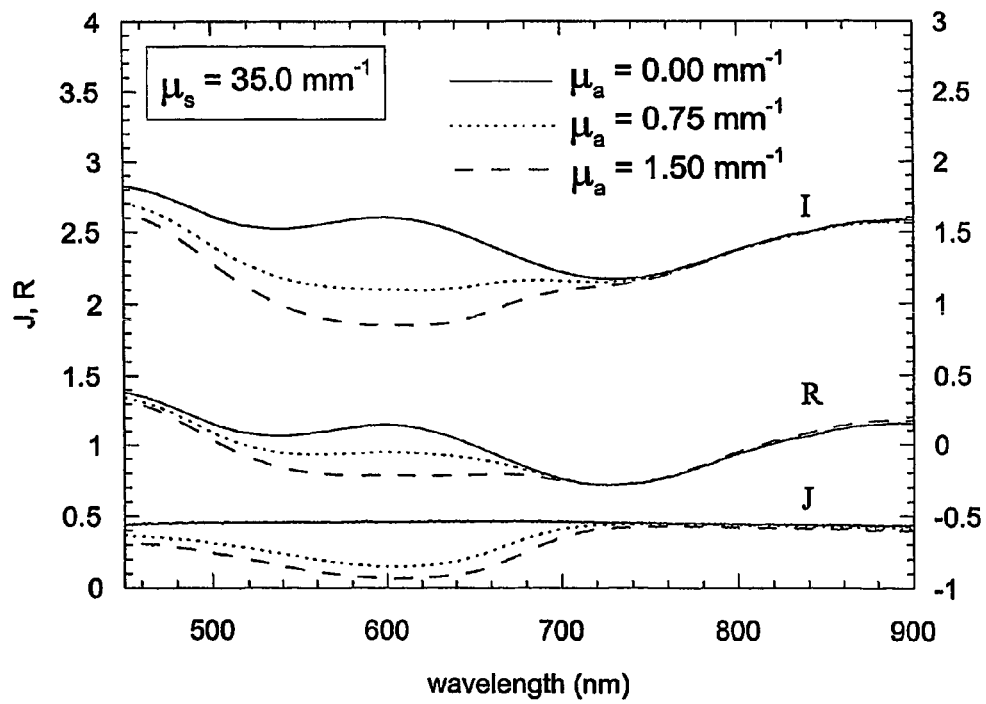
FIG. 8 is a graph of measurement results for three different absorption coefficients $\mu_a$ showing the dc-fiber signal I, the c-fiber signal J and the differential backscatter signal $R_{bs}$ as a function of wavelength.

In the following, the effect of absorption on the average path length τ will been examined in more detail. Various concentrations of Evans Blue dye were added to a suspension of polystyrene spheres with scattering coefficients $\mu_s$ of 35 $mm^{-1}$. The concentrations of Evans Blue (EB) dye were varied such that the absorption coefficient $\mu_a$ at 600 nm was in the range of 0 to 2 $mm^{-1}$. Typical results of the differential backscatter signal $R_{bs}$ for three different absorption coefficients $\mu_a$ are shown in FIG. 8. Note that the signal I of the dc-fiber 5 is plotted on a different vertical scale than the signal J of the c-fiber 6 and the differential backscatter signal $R_{bs}$.

The spectra with Evans Blue $R^{EB}$ present in the suspension were divided by the spectrum with no Evans Blue present $R^0$ and the negative natural logarithm of the ratio $R^{EB}/R^0$ was determined:

$$A = -\ln(R^{EB}/R^0) = \tau \cdot \rho \cdot \mu_a^{spec,EB} \tag{11}$$

where ρ is the concentration of Evans Blue, and $\mu_a^{spec,EB}$ is the specific absorption coefficient of Evans Blue.

Figure 9:
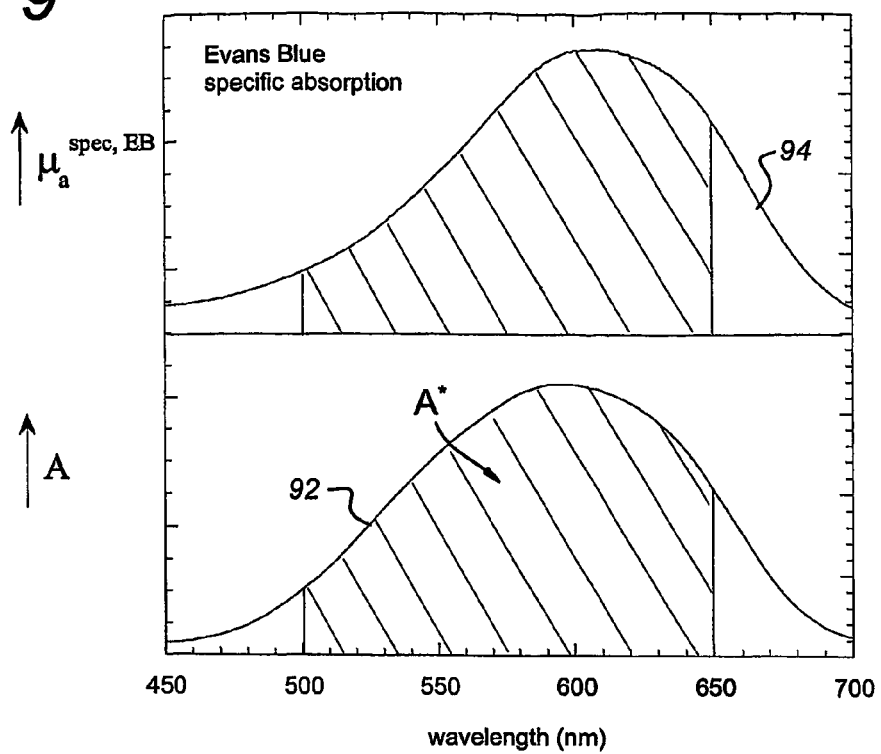
FIG. 9 shows a typical spectrum of an absorption curve A along with the specific absorption coefficient of Evans Blue dye.

FIG. 9 shows a typical spectrum of an absorption curve 92, along with the specific absorption coefficient $\mu_a^{spec,EB}$ of Evans Blue dye, see curve 94.

For all concentrations, an area A* under the absorption curve 92 was determined in the wavelength range λ between 500 and 650 nm. From Eq. (11) it follows that if the average path length τ is independent of the absorption coefficient $\mu_a^{spec}$, area A* should depend linearly on the concentration p of the species in the suspension.

Figure 10:
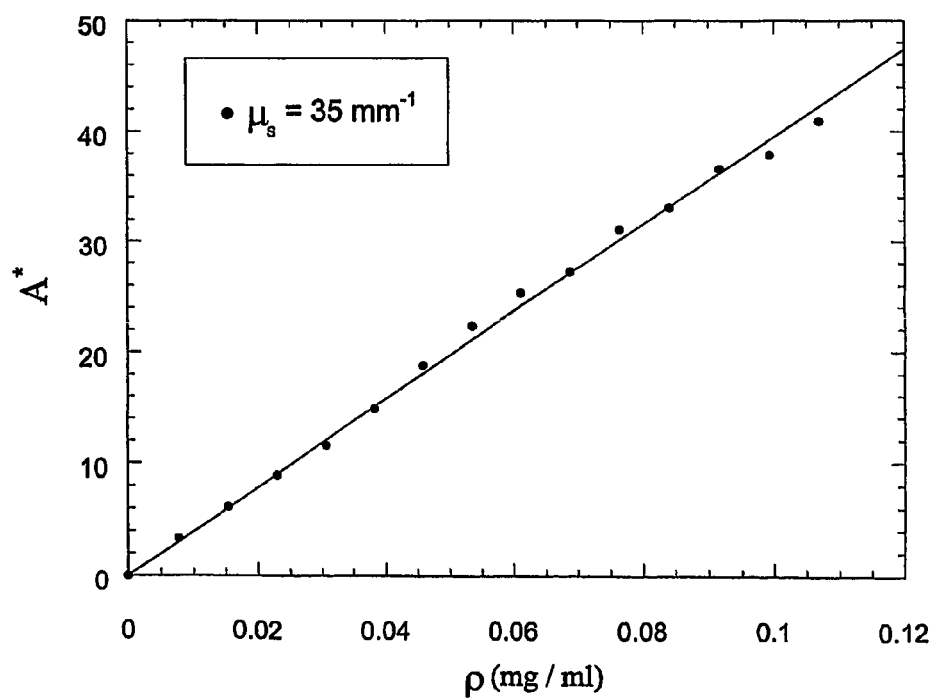
FIG. 10 shows a measured A* as a function of the absorption coefficient $\mu_a$ at λ=600 nm.

FIG. 10 shows a measured A* as a function of the absorption coefficient $\mu_a$ at 600 nm. A curve fitting is done, resulting in a line 104 for $\mu_s(\lambda)=35$ $mm^{-1}$. FIG. 10 shows that the average path length τ is indeed independent of the absorption coefficient $\mu_a$ in the range 0-2 $mm^{-1}$.

Figure 11:
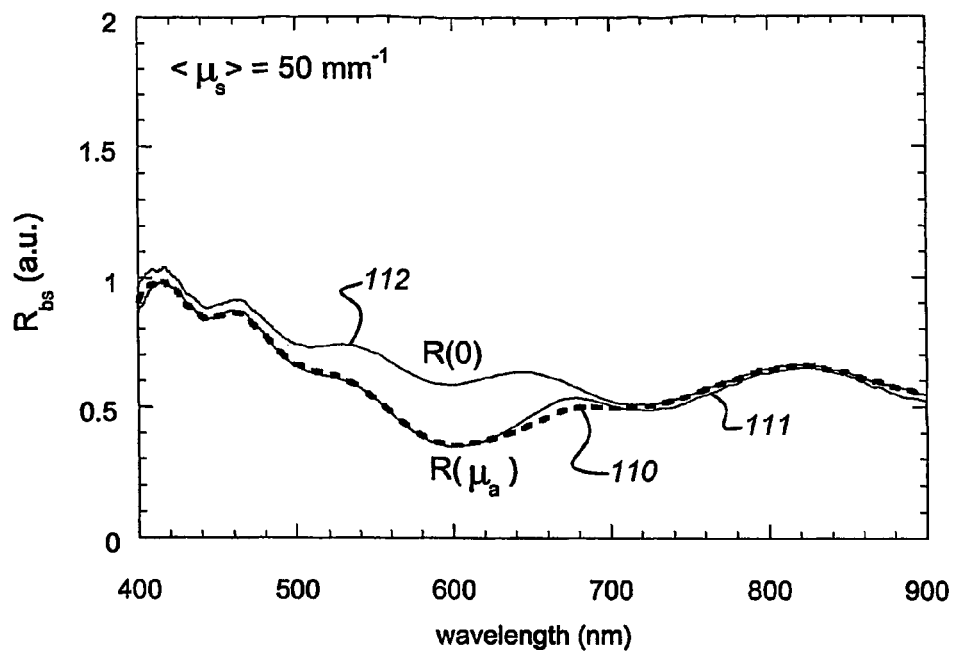
FIG. 11 shows typical spectra measured in a suspension of 1.0 μm polystyrene spheres with and without Evans Blue dye.

From the previous results of FIGS. 4 to 10, it shows that for mfp<$d_{fiber}$, the differential backscatter signal $R_{bs}$ is described by Eq. (7) with $C_2 \approx 0.6$. FIG. 11 shows typical spectra measured in a suspension of 1.0 μm polystyrene spheres with and without Evans Blue dye ($\mu_z$=2 and 0 $mm^{-1}$ at 600 nm, respectively). From Eq. (7) and FIG. 7, the relation between the differential backscatter signals with and without absorber is given by $$R_{bs}(\lambda,\mu_a) = R_{bs}(\lambda,0) \cdot \exp(-0.24 \cdot \mu_a) \tag{12}$$

The calculated spectrum according to Eq. (12) is plotted as a dashed line 110 in FIG. 11 and shows excellent agreement with the measured $R_{bs}(\lambda,\mu_a)$, see line 111. In FIG. 11, line 112 depicts $R_{bs}(\lambda,0)$.

In short, the average path length τ of photons measured when subtracting the signals of the c-fiber 6 from the dc-fiber 5 using Eq. (1) is independent of the optical properties of the sample 1 and approximately equal to half the diameter of the fibers 5, 6 used, as long as the fiber diameter is larger than the mfp.

In a specific embodiment, the device according to the invention is arranged to determine concentrations of oxygenated blood in tissue. Since the scattering coefficient of tissue $\mu_s^{tissue}$ is in the range of 10-100 $mm^{-1}$, the fiber diameter should be smaller than a certain maximum diameter $d_{max}$ where $d_{max}$ is between 10 and 100 μm, for example, smaller than 50 nm, in order to measure predominantly single scattering in tissue. In this case, Eq. (5) holds. For fibers 5, 6 with much larger diameters (e.g. 200 or 400 μm), the differential backscatter signal $R_{bs}(\lambda)$ is described by Eq. (10) with $\tau \approx 0.6 \cdot d_{fiber}$.

It is presently known that the wavelength dependence of the scattering coefficient in tissue $\mu_s^{tissue}$ can be adequately described by an empirical power-law function, see also the van de Hulst article cited herein, as well as A. Angstrom, "On the Atmospheric Transmission of Sun Radiation and on Dust in the Air", Geograf. Ann. Deut. 11, pp. 156-166 (1929); and R. Graaff, J. G. Aarnoudse, J. R. Zijp, P. M. A. Sloot, F. F. M. de Mul, J. Greve, and M. H. Koelink, "Reduced Light-Scattering Properties for Mixtures of Spherical Particles: A Simple Approximation Derived from Mie Calculations", Applied Optics. 31, pp. 1370-1376 (1992).

$$\mu_s^{tissue}(\lambda) = a \cdot \lambda^{-b} \tag{13}$$

with a and b constants that depend on the size, concentration and relative refractive index of the scatterers (i.e. substances) present in the detection volume.

The dominant absorbers in tissue in the visible wavelength range are oxygenated and deoxygenated blood. Thus in tissue Eq. (10) becomes $$\begin{aligned} R_{bs}(\lambda) &= C_{app} \cdot a\lambda^{-b} \cdot \exp(-0.6 \cdot d_{fiber} \cdot \rho_{blood} \cdot \\ &\quad (S_{O2} \cdot \mu_a^{spex.ox} + (1-S_{O2}) \cdot \mu_a^{spex.deox})) \\ &= C'_{app} \cdot \lambda^{-b} \cdot \exp(-0.6 \cdot d_{fiber} \cdot \rho_{blood} \cdot \\ &\quad (S_{O2} \cdot \mu_a^{spex.ox} + (1-S_{O2}) \cdot \mu_a^{spex.deox})) \end{aligned} \tag{14}$$

where $\rho_{blood}$ is the concentration of blood, $S_{O2}$ is the blood oxygenation (percentage oxygen saturation) in a certain detection volume, $C_{app}$ is a constant that depends on the calibration constant c, $C'_{app}$ is $C_{app} \cdot a$, λ is the wavelength, b is the slope of the scattering coefficient defined in Eq. 13, $\mu_a^{spec,ox}$ is the specific absorption coefficients of fully oxygenated blood, and $\mu_a^{spec,deox}$ is the specific absorption coefficients of fully deoxygenated blood.

Non-linear phenomena such as an inhomogeneous distribution of absorbers are not incorporated in Eq. (14), but can be added by the skilled person.

Figure 12:
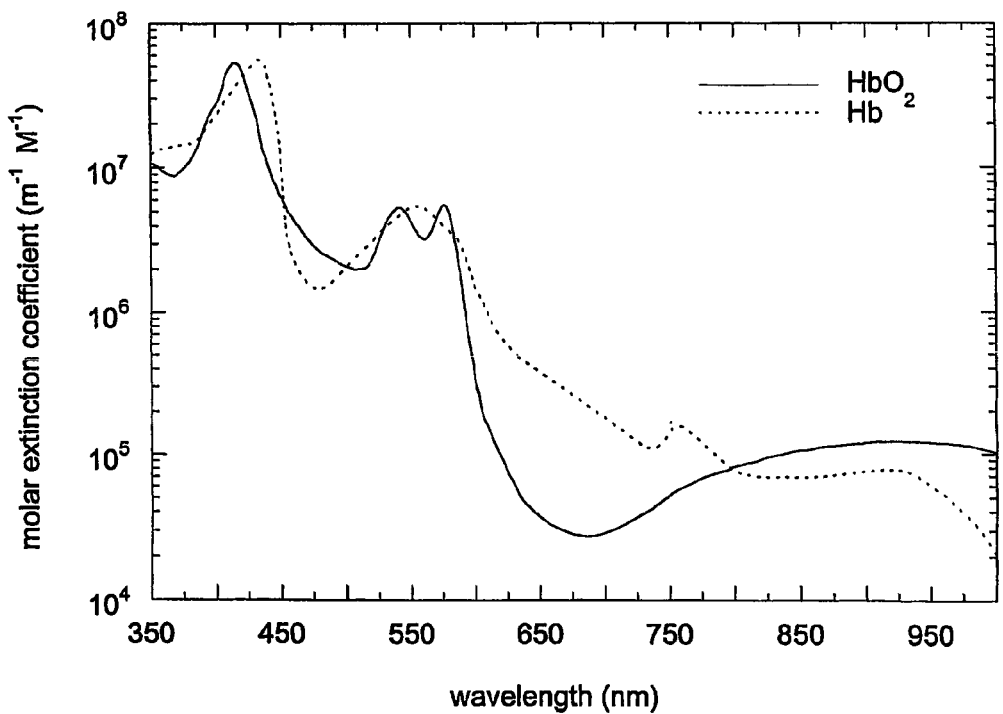
FIG. 12 graphically shows a molar extinction coefficient as a function of wavelength.

Since the specific absorption coefficients of fully oxygenated ($\mu_a^{spec,ox}$) and fully deoxygenated ($\mu_a^{spec,deox}$) blood are well known, see FIG. 12, Eq. (14) can be fitted to the measured data to yield the slope b of the scattering coefficient $\mu_s^{tissue}$, the concentration $\rho_{blood}$ and the oxygen saturation $S_{O2}$ of the blood present in the detection volume. When a correction is made for the inhomogeneous distribution of blood in the vessels, a vessel diameter D may be determined as well. Since the average detection depth is small (e.g. 0.1 mm), the blood present in the detection volume when measuring non-invasively is located in capillaries.

Figure 13:
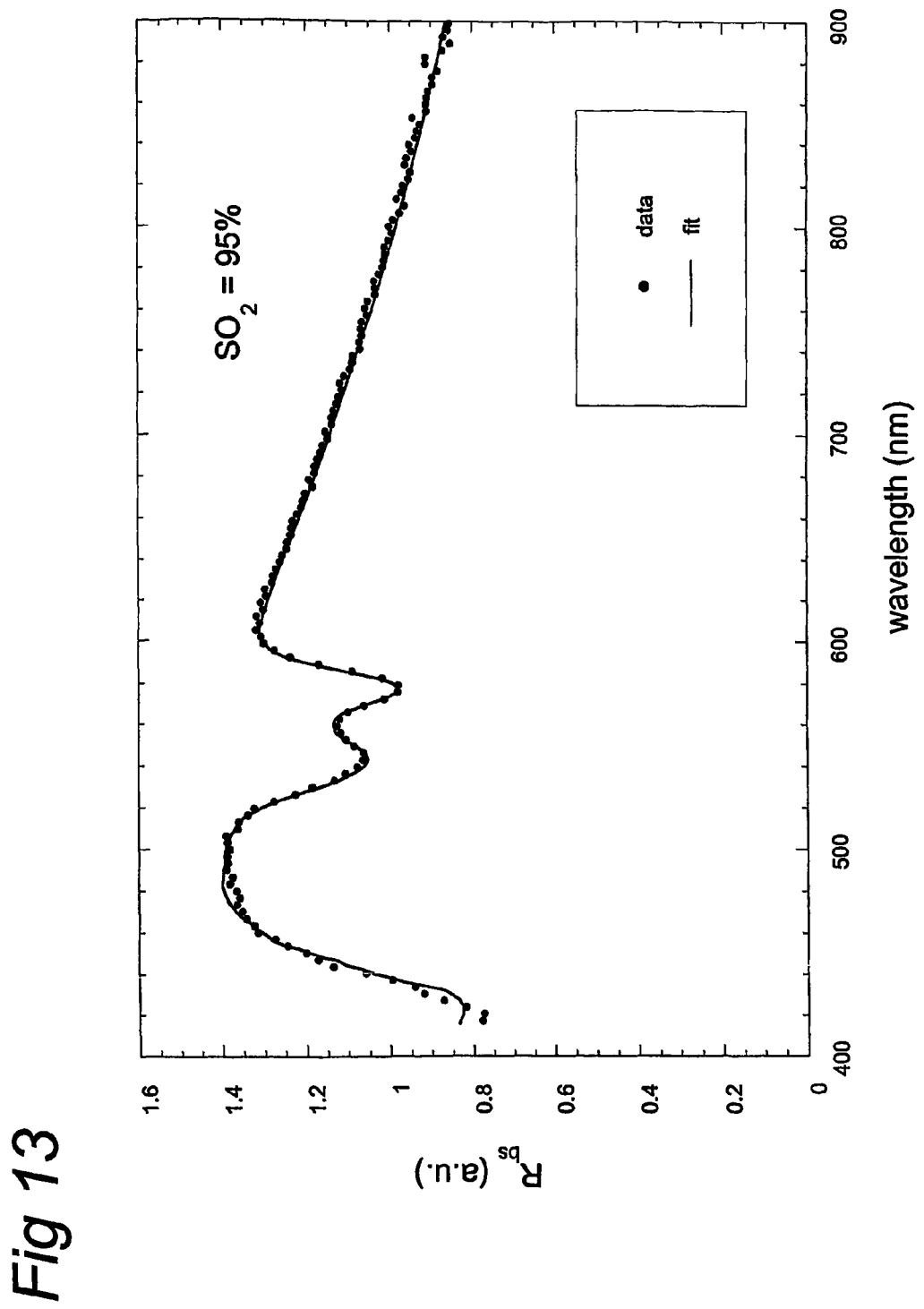
FIG. 13 shows in vivo measurements and a fit of the differential backscatter signal $R_{bs}$ in a human trachea realized using a fiber diameter of 400 μm.

In FIG. 13, in vivo measurements of backscattering in a human trachea together with a fit using Eq. (14) are shown. The measurements are realized using a fiber diameter of 400 μm. The dots depict the measurements and curve 130 is a fitting curve. In FIG. 13, b=−0.94 and the oxygenation $S_{O2}$=95%.

The present invention can be used for tumor detection. Tumor growth may, due to its excessive oxygen consumption, be accompanied by a low capillary oxygen saturation, which can only be assessed using a very localized measurement. Since (pre-)cancerous tissue is generally more heterogeneous than normal tissue, the standard deviation of multiple measurements is likely to be larger for (pre-)cancerous tissue than for normal tissue. Standard deviations in the measurements can be calculated for the oxygen saturation, the blood concentration, the blood vessel diameter, and the slope b of the scattering coefficient $\mu_s^{tissue}$. It is noted that the invention is by no means restricted to determine a concentration of a substance as the physical feature. All features, mentioned in the previous phrase can be regarded as physical features.

Figure 14:
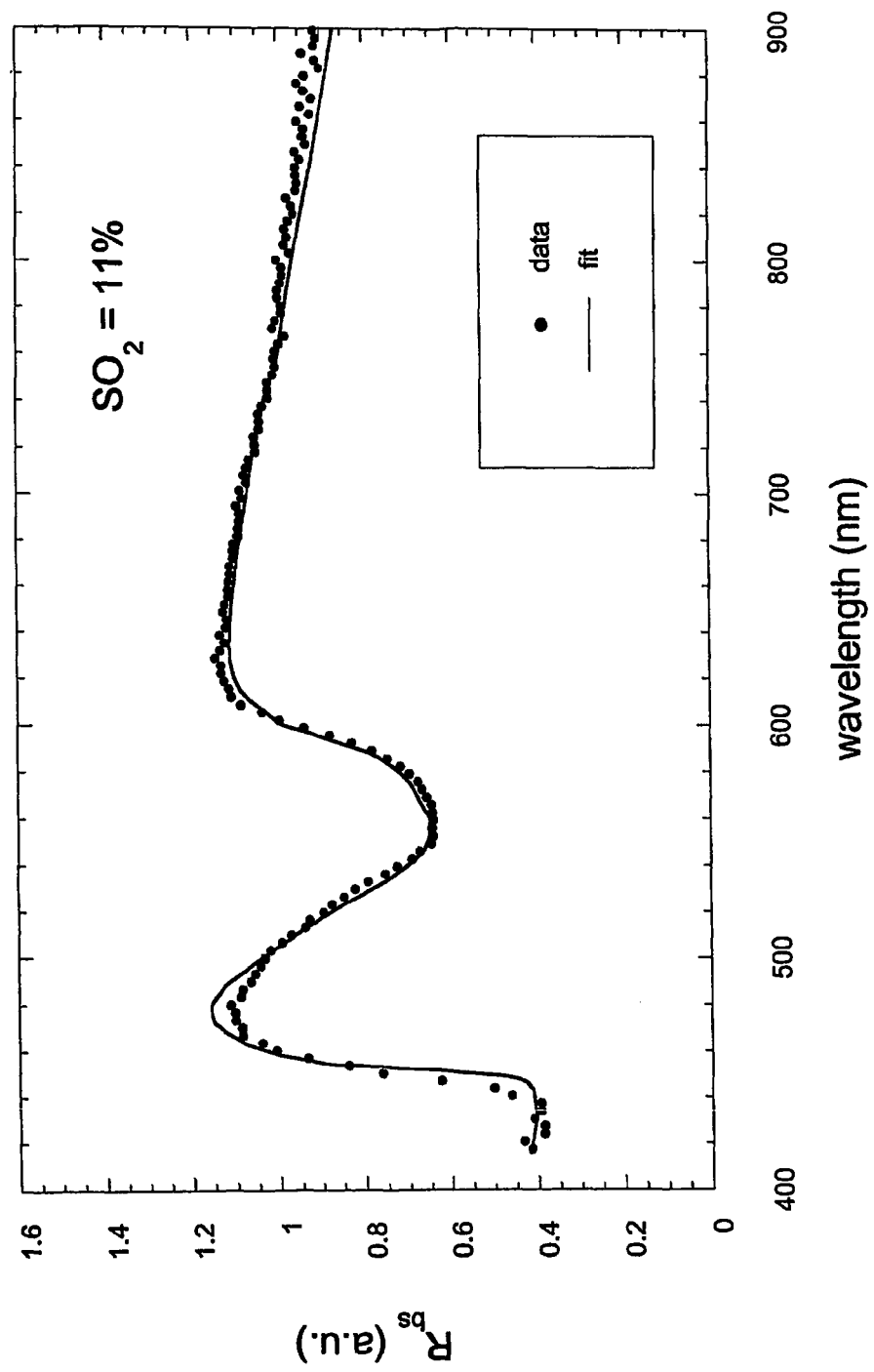
FIG. 14 shows in vivo measurements and a fit of the differential backscatter signal $B_{bs}$ in a human trachea showing very low oxygenation indicative for lung tumor.

An example of a measurement of a lung tumor is shown in FIG. 14. The shape of the dip in the wavelength range of 500-600 nm in this figure demonstrates the depletion of oxygen from the capillaries of this tumor due to its excessive oxygen consumption.

When a needle-probe is used, the local oxygenation and scattering coefficient $\mu_s^{tissue}$, can be measured invasively. This could be helpful in determining tumor-margins intra-operatively in real-time, for instance during resection of a breast-tumor.

According to an embodiment, the device comprises multiple probes and a multichannel spectrometer for multiple simultaneous measurements on different locations of the sample (1). Using this device, multiple measurements can be made simultaneously on different locations of for example a suspicious lesion.

In yet another embodiment, the device comprises at least two pairs of fibers, having different fiber diameters. For example, when a pair of fibers with 100 µm, a pair of fibers with a diameter of 200 µm and a pair of fibers with a diameter of 400 µm are used, information from different depths in the sample 1 can be obtained as the average path length increases with increasing fiber diameter.

The method and apparatus according to the invention can also be used to analyze local drug concentrations. From Eq. (10) it follows that if the specific absorption coefficient of a certain drug is known, the local concentration p of that substance can be determined using the invention.

Another possibility of the present invention is to monitor glucose concentrations. The scattering coefficient $\mu_s^{tissue}$ depends among others on the relative refractive index of the scatterers with respect to the surrounding medium (in tissue: cytoplasm). The refractive index of the surrounding cytoplasm is likely to depend on the concentration of glucose. A change in the glucose concentration will therefore likely affect the slope b of the scattering coefficient tissue $\mu_s^{tissue}$, Eq. (13).

While specific embodiments of the invention have been described above, it will be appreciated that the invention may be practiced otherwise than as described. For example, a concentration of a substance in polluted water may be calculated. The description is not intended to limit the scope of the invention.

The invention claimed is:

1. A device for determining a physical feature of a sample (1), comprising:
   a light source (2) for producing radiation;
   a probe with at least a first and a second optical fiber (5, 6), the first optical fiber (5) having a first diameter and being arranged to deliver the radiation on a sample (1) and to collect first backscattered radiation from the sample (1), the second optical fiber (6) having a second diameter and being arranged to collect second backscattered radiation, wherein the second optical fiber (6) is positioned alongside the first optical fiber (5); wherein at least one of said fibers both delivers light from the light source and measures scattered light from the sample (1);
   a spectrometer (7) for producing a first signal (I) based on the first backscattered radiation, and for producing a second signal (J) based on the second backscattered radiation;
   a processor (9) arranged to determine a measured differential backscatter signal as a function of wavelength (λ) using the first and second signals (I, J), wherein the processor is arranged to calculate the physical feature.

2. The device according to claim 1, wherein the device is configured for:
   simultaneously measuring backscatter radiation on different locations of the sample (1);
   determining a physical feature for the different locations; and
   calculating a standard deviation of the physical feature.

3. The device according to claim 1, wherein the physical feature is a concentration of at least one substance in the sample (1).

4. The device according to claim 1, wherein the processor is arranged to calculate the physical feature by curve fitting the measured differential backscatter signal to a backscatter function ($R_{bs}$), wherein the backscatter function is a function of a mean free path of photons.

5. A method of determining a physical feature of a sample (1), comprising the steps of:
   producing radiation with a light source (2);
   placing a probe on a sample (1), the probe comprising a first optical fiber (5) having a first diameter, and at least a second optical fiber (6) having a second diameter;
   sending light coming from the light source, through the first optical fiber;
   collecting first backscattered radiation through the first optical fiber and second backscattered radiation through the second optical fiber; wherein at least one of said fibers both delivers light from the light source and measures scattered light from the sample (1);
   producing a first signal (I) based on the first backscattered radiation, and a second signal (J) based on the second backscattered radiation;
   determining a measured differential backscatter signal as a function of wavelength using the first and second signals (I, J); and
   calculating the physical feature.

6. A method according to claim 5, wherein the physical feature is calculated by curve fitting the measured differential backscatter signal to a backscatter function, in which the backscatter function is a function of a mean free path of photons.

7. The method according to claim 6, wherein the backscatter function ($R_{bs}$) is defined by:

$$R_{bs}(\lambda) = C'_{app} \cdot p(\lambda, 180) \cdot \mu_s(\lambda) \cdot \exp(-2 \cdot mfp(\lambda)) \cdot \sum_{i=1}^{n} p_i \cdot \mu_a^{spec,i}(\lambda))$$

where $C_{app}'$ is an apparatus constant, $p(\lambda,180)$ is a phase function, $\mu_s(\lambda)$ is a scattering coefficient of the sample (1), λ is a wavelength of the first and second backscattered radiation, mfp(λ) is the mean free path as a function of the wavelength, n is a number of substances in the sample (1), is concentration of absorber i present in a detection volume of the sample (1), and $\mu_a^{spec,i}(\lambda)$ is an absorption coefficient of substance i as a function of the wavelength.

8. The method according to claim 6, wherein the method further comprises the steps of:
   simultaneously measuring backscatter radiation on different locations of the sample (1);
   determining a physical feature for the different locations; and
   calculating a standard deviation of the physical feature.

9. A method according to claim 5, wherein the fibers are positioned alongside one another.

10. The method according to claim 5, wherein the physical feature is calculated by curve fitting the measured differential backscatter signal to a backscatter function, in which the backscatter function is a function of an average path-length ($\tau$) traveled by detected scattered photons, the average path-length ($\tau$) being independent from an absorption coefficient ($\mu_a$) of the sample (1), and from a scattering coefficient ($\mu_s$) of the sample.

11. The method according to claim 10, wherein the average path-length ($\tau$) is also independent from a wavelength ($\lambda$) of the first and second backscattered radiation.

12. The method according to claim 10, wherein the path-length ($\tau$) is proportional to the first fiber diameter.

13. The method according to claim 10, wherein the backscatter function is given by:

$$R_{bs} = C_1 \cdot \mu_s \cdot \exp(-\tau \cdot \mu_a)$$

with $\tau = C_2 d_{fiber}$ where $C_1$ and $C_2$ are constants, $\mu_a$ is the absorption coefficient of the sample (1), $\mu_s$ is the scattering coefficient of the sample (1), and $d_{fiber}$ is the first fiber diameter.

14. The method according to claim 13, wherein $C_2$ is approximately 0.6.

15. The method according to claim 10, wherein the physical feature is a concentration of at least one substance in the sample (1).

16. The method according to claim 10, wherein the method further comprises the steps of:

simultaneously measuring backscatter radiation on different locations of the sample (1);

determining a physical feature for the different locations; and calculating a standard deviation of the physical feature.

* * * * *